United States Patent
Zhao et al.

(10) Patent No.: US 8,193,162 B2
(45) Date of Patent: Jun. 5, 2012

(54) HUMAN LIVER REGENERATION ASSOCIATED PROTEIN AND THE USE THEREOF

(75) Inventors: Mujun Zhao, Shanghai (CN); Zhanwu Liu, Shanghai (CN); Jie Qiu, Shanghai (CN); Zaiping Li, Shanghai (CN)

(73) Assignee: Shanghai Institutes for Biological Sciences, CAS, Shanghai (CN)

( * ) Notice: Subject to any disclaimer, the term of this patent is extended or adjusted under 35 U.S.C. 154(b) by 0 days.

(21) Appl. No.: 12/766,613

(22) Filed: Apr. 23, 2010

(65) Prior Publication Data

US 2010/0203065 A1    Aug. 12, 2010

Related U.S. Application Data

(62) Division of application No. 10/541,247, filed as application No. PCT/CN03/01154 on Dec. 31, 2003, now Pat. No. 7,741,468.

(30) Foreign Application Priority Data

Jan. 3, 2003    (CN) .................................. 03 1 14718

(51) Int. Cl.
  *A61K 48/00* (2006.01)
  *C07H 21/04* (2006.01)
  *C07H 21/02* (2006.01)
  *C07K 16/00* (2006.01)
(52) U.S. Cl. ...... 514/44; 536/23.1; 536/24.5; 530/387.1
(58) Field of Classification Search .................. None
  See application file for complete search history.

*Primary Examiner* — Amy Bowman
(74) *Attorney, Agent, or Firm* — Osha • Liang LLP (57) ABSTRACT

This invention provides a novel human liver regeneration associated protein hLRTM4 and the polynucleotide which encodes the hLRTM4 protein. Furthermore, this invention provides a method of preparing and using hLRTM4 protein, and its polynucleotides. hLRTM4 protein can be used to treat liver injury, and its antagonists (e.g. antisense nucleic acids and antibodies) can be used to treat hepatocellular carcinoma. This invention also provides the corresponding pharmaceutical compositions.

8 Claims, 2 Drawing Sheets

7404Control     7404+LR+     7404+LR−

HUMAN LIVER REGENERATION ASSOCIATED PROTEIN AND THE USE THEREOF

CROSS REFERENCE TO RELATED APPLICATIONS

This is a divisional application of U.S. patent application Ser. No. 10/541,247 filed on Jul. 1, 2005, which is a national stage application of PCT application No. PCT/CN03/01154, filed on Dec. 31, 2003, which claims the priority of Chinese Patent Application No. 03114718.6, filed on Jan, 3, 2003. These prior applications are incorporated by reference in their entirety.

FIELD OF INVENTION

The invention belongs to the fields of molecular biology and medical science. In detail, the invention relates to a novel human liver regeneration associated protein hLRTM4 and its coding sequence. It also relates to the preparation and application of hLRTM4 polynucleotide and polypeptide.

TECHNICAL BACKGROUND

Liver has a remarkable capacity to regenerate. After partial hepatectomy or physical, chemical injury, liver starts to regenerate until the liver mass reaches to correct size. Liver regeneration is associated with many liver diseases, such as liver cirrhosis and acute/chronic hepatitis. The progression of hepatocellular carcinoma often accompanies with liver regeneration. Meanwhile, liver regeneration is also implied in partial liver transplantation and hepatocyte transplantation in clinical use.

Hepatocellular carcinoma (HCC) is the fifth most common malignancy in the world. China is a high-incidence area of HCC. It is estimated to cause approximately 250,000 deaths annually worldwide, 40% of which is in China (Shaobai Li. "Hepatology", People's Medical Publishing House, 2002). Because of its high fatality, the incidence and mortality rates are almost equal. The major factors to cause HCC are chronic hepatitis B virus (HBV) infection, chronic hepatitis C virus (HCV) infection, alcoholic cirrhosis and exposure to hepatotoxins like aflatoxin in food and water supplies. Recent studies suggest that the progression of HCC and liver regeneration are closely related: Liver regeneration is a well-regulated hepatocyte proliferation in normal situation, but becomes out of control in HCC. Some hypothesis suggests that process of HCC progression is as follows: liver injury caused by virus infection or toxic chemicals leads to the consequent liver regeneration; chronic injury causes the whole process recur many times and finally becomes out of control, and in the end results in HCC. Thus, understanding the relationship between HCC and liver regeneration will help us to predict and provide treatment for early hepatocellular carcinoma.

Nowadays, the most efficient way to treat several liver diseases is liver transplantation, whose technique is well established. However, the number of donor organs and the problem of immune exclusion inherently limit liver transplantation at present time. Main methods to resolve these two problems are partial liver transplantation and hepatocyte transplantation. Partial liver transplantation enables one donor liver to transplant into two or more patients and gives chance to transplant liver between relatives in order to reduce the immune exclusion. Another optimizing way is hepatocyte transplantation, which is to directly transplant hepatocytes into liver or spleen of patients. The transplanted hepatocytes then integrate into the recipient organs, begin to re-proliferate and perform the function of liver. Hepatocyte transplantation can use hepatocytes from the patients themselves in order to avoid immune exclusion. Both methods utilize the regenerative capacity of liver, but the protein factors essential to liver regeneration and the mechanism of liver regeneration are still unknown.

To meet the needs of liver transplantation and HCC treatment, There is an urgent need in the art to know the factors related to liver regeneration, especially the genes and proteins associated with liver regeneration.

SUMMARY OF INVENTION

The aim of the present invention is to offer a novel liver regeneration associated protein hLRTM4 and its fragments, analogs and derivatives.

The second aim of the present invention is to offer the polynucleotides that encode these polypeptides.

The third aim of the present invention is to offer the method of producing these polypeptides and the application of these polypeptides and coding sequences. The hLRTM4 gene herein relates to liver regeneration and carcinogenesis. This important observation has not been reported before. Research of the molecular mechanism of hLRTM4 will help us to elucidate the molecular and biological mechanism of liver regeneration, and provide potential treatment for liver diseases.

In the first aspect, the invention provides a pharmaceutical composition, which comprises a safe and effective amount of human liver regeneration associated protein hLRTM4, and a pharmaceutically acceptable vehicle, diluent or carrier.

Preferably, the hLRTM4 protein has the amino acid sequence as shown in SEQ ID NO:2

In a preferred embodiment, the safe and effective amount of hLRTM4 is 1 ug-5 mg/kg body weight per day.

In the second aspect, the invention provides a use of hLRTM4 protein in the preparation of drugs for therapeutic treatment of liver injury.

Preferably, the drugs are used to treat liver diseases caused by acute/chronic hepatitis, liver cirrhosis or liver cancer.

In the third aspect, this invention provides a pharmaceutical composition, which comprises a safe and effective amount of antagonists of hLRTM4 protein, wherein the antagonists are selected from the group consisting of: (i) an antisense polynucleotide to hLRTM4, wherein the polynucleotide has the antisense nucleotide sequence as shown in SEQ ID NO: 1 and has a length of 15-625 bp, and/or (ii) a specific antibody against hLRTM4, as well as a pharmaceutically acceptable vehicle, diluent or carrier.

Preferably, the nucleic acid molecule has the full-length antisense sequence to SEQ ID NO:1.

In another preferred example, the safe and effective amount of hLRTM4 is 1 ug-5 mg/kg body weight per day.

In the fourth aspect, the invention provides a use of antagonist to hLRTM4, wherein the antagonist is selected from: (i) an antisense polynucleotide to hLRTM4, wherein the polynucleotide has the nucleotide sequence as shown in SEQ ID NO: 1 and has a length of 15-625 bp; (ii) a small interfering double-strand RNA of hLRTM4, wherein the RNA has the nucleotide sequence as shown in SEQ ID NO:1 and has a length of 17-23 by and a 3'-terminal dtdt sequence; and/or (iii) a specific antibody against hLRTM4. These antagonists are used to prepare drugs for treatment of hepatocellular carcinoma.

Preferably, the antagonists are antisense polynucleotides to hLRTM4, wherein the polynucleotides has the nucleotide sequence as shown in SEQ ID NO: 1 and has a length of 15-625 bp.

In another preferred embodiment, the small interfering double-strand RNAs has one of the nucleotide sequences as shown in SEQ ID NO: 9-13.

The other aspects of the invention will be apparent to the skilled in the art in light of the technical disclosure of the invention.

DESCRIPTION OF DRAWINGS

BEL-7404 is a kind of hepatoma cell, BEL-7404/pcDNA3 refers to BEL-7404 cell transfected with pcDNA3 vector, BEL-7404/LR+ refers to BEL-7404 cell transfected with sense hLRTM4 gene, BEL-7404/LR− refers to BEL-7404 cell transfected with antisense hLRTM4 gene. All the cells mentioned above were synchronized 24 h in serum-free DMEM medium, then seeded into 24-well plates at $5.0 \times 10^3$ cells per well. Cell growth was measured using a 3-[4,5-dimethylthiazol-2-yl]-2,5-diphenyltetrazolium bromide (MTT) method during 8 days, n=6.

BEL-7404 cells were subcutaneously injected to 5-week-old nude mice to generate tumors. Different plasmids were then introduced by tail vein as indicated. Group 1, control group, without any treatment after tumor generation (7404 control); group2, intravenously injected pcDNA3LR+ plasmid after tumor regeneration (7404+LR+); group 3, intravenously injected pcDNA3LR− plasmid after tumor regeneration (7404+LR−).

The $CCl_4$ liver injury model is used. Group 1, normal rats; group 2, rats administrated with 0.5 ml $CCl_4$/kg body weight; group 3, rats administrated with 1 ml $CCl_4$/kg body weight. In group 2 and group 3, the black columns indicate the introduction of hLRTM4 gene. Results indicates that the level of glutamate pyruvate transaminase (GPT) is low in normal liver tissue, but raised after $CCl_4$ administration in a dose dependent manner. After the introduction of hLRTM4 gene, the GPT level decreased. These results suggested that hLRTM4 gene was effective in repairing liver injury.

DETAILED DESCRIPTION OF INVENTION

The inventors cloned the human hLRTM4 gene from human liver cDNA library. The gene has 87% identity with the rat LRTM4 gene which was reported and applied for patent by us. The searching results in the DNA sequence database indicated that the sequence content of hLRTM4 gene was similar to the il-TMP gene, which was found and cloned in human intestinal epithelium cell in 1995. The hLRTM4 gene is 1362 bp, including a 606 bp ORF, which encodes a 202aa protein. hLRTM4 protein is a transmembrane 4 superfamily member and is closely related to liver regeneration. Animal experiments proved that it could be used to promote liver regeneration and repair liver injury.

This invention also proved that hLRTM4 gene was overexpressed in hepatocellular carcinoma cells and could be considered as a molecular marker in HCC diagnosis. Furthermore, the antisense polynucleotide of hLRTM4 inhibits the proliferation of HCC cells and the growth of solid tumor in nude mice models. Thus, antagonists to hLRTM4 (antisense polynucleotides, antibodies, etc.) can be used in tumor treatment, especially for hepatocellular carcinoma.

In the present invention, the terms "hLRTM4 protein", "hLRTM4 polypeptide" or "liver regeneration associated protein hLRTM4", are exchangeable, referring to a protein or polypeptide comprising the amino acid sequence of liver regeneration associated protein hLRTM4 (SEQ ID NO: 2). The term includes hLRTM4 protein with or without the starting Met residue, The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated.

As herein described, "isolated hLRTM4 protein or polypeptide" refers to hLRTM4 polypeptide essentially free from contaminating cellular components, such as carbohydrate, lipid, or other proteinaceous impurities associated with the polypeptide in nature. The technical personnel in the art can purify hLRTM4 protein with standard protein purification techniques.

The polypeptides of the present invention can be recombinant polypeptides, nature polypeptides, synthesized polypeptides, and preferably recombinant polypeptides. The polypeptides of the present invention can be naturally purified products, or chemically synthesized products, or recombinant products from prokaryotic or eukaryotic hosts (e.g. bacteria, yeast, higher plant, insect or mammalian cell). The polypeptides of the present invention can be glycosylated or non-glycosylated according to the different hosts used.

The present invention further relates to the fragments, derivatives and analogs of hLRTM4 protein.

The polynucleotide of invention may be in the forms of DNA and RNA. DNA includes cDNA, genomic DNA, and synthetic DNA, etc., in single strand or double strand form. A single strand DNA may be an encoding strand or non-encoding strand. The coding sequence for mature polypeptide may be identical to the coding sequence shown in SEQ ID NO:1, or is a degenerate sequence. As used herein, the term "degenerate sequence" means an sequence which encodes a protein comprising the sequence of SEQ ID NO: 2 and which has a nucleotide sequence different from the coding region in SEQ ID NO:1.

The present invention further relates to polynucleotides, which hybridize to the hereinabove-described sequences. As proved in the present invention by experiments, antisense hLRTM4 can be used to inhibit tumor growth. As herein described, the "polynucleotide fragments" may have at least 15 bases, preferably at least 30 bases, more preferably at least 50 bases and most preferably at least 100 bases which hybridize to a polynucleotide of the present invention. These polynucleotides can be used to identify and/or isolate polynucleotides encoding hLRTM4 protein by nucleotide amplification techniques like PCR.

The full-length hLRTM4 nucleotide sequence or its fragment can be prepared by PCR amplification, recombinant method and synthetic method. For PCR amplification, one can obtain said sequences by designing primers based on the nucleotide sequence disclosed herein, especially the ORF, and using cDNA library commercially available or prepared by routine techniques in the art as a template. When the sequence is long, it is usually necessary to perform two or more PCR amplifications and link the amplified fragments together correctly.

Once the sequence is obtained, one can produce lots of the sequences by recombinant methods. Usually, said sequence is cloned into a vector which is then transformed into a host cell. The sequence is isolated from the amplified host cells using conventional techniques.

Further, the sequence can be synthesized, especially when the fragments are short. Typically, several small fragments are synthesized and linked together to obtain a long sequence.

The present invention also includes vectors and expression vectors comprising the polynucleotides described hereinabove. The present invention further includes genetically engineered recombinant host cells containing these expression vectors or the encoding sequence of hLRTM4 protein, and methods for producing the polypeptides hereinabove by recombinant technologies.

Host cells can be transformed with the recombinant DNAs by general technique known to all the technicians in the art. The transformants can be cultured by general methods and express polypeptides encoded by gene of this invention. According to the used host cells, the medium for cultivation can be selected from various conventional mediums. The host cells are cultured under a condition suitable for its growth until the host cells grow to an appropriate cell density. Then, the selected promoter is induced by appropriate means (e.g., temperature shift or chemical induction) and cells are cultured for an additional period.

In the above methods, the recombinant polypeptide may be included in the cells, or expressed on the cell membrane, or secreted out. If desired, the physical, chemical and other properties can be utilized in various isolation methods to isolate and purify the recombinant protein. These methods are well-known to the artisans and include, but are not limited to conventional renaturation treatment, treatment by protein precipitant (e.g., salt precipitation), centrifugation, cell lysis by osmosis, sonication, supercentrifugation, molecular sieve chromatography or gel chromatography, adsorption chromatography, ion exchange chromatography, HPLC, and any other liquid chromatography, and the combination thereof.

The recombinant hLRTM4 proteins or polypeptides have various uses including, but not to be limited to: treat diseases which are caused by the loss or depression of the hLRTM4 protein function (especially to promote the recovery of injured liver); screen for antibodies, polypeptides or other ligands which can activate or inhibit the function of hLRTM4 protein. Screening the polypeptide library with expressed recombinant hLRTM4 protein will help us to find the polypeptides with therapeutic potential, which can inhibit or activate the function of hLRTM4.

In another aspect, the present invention includes the polyclonal antibodies and monoclonal antibodies with specificity to polypeptides encoded by hLRTM4 DNA or its fragments, especially monoclonal antibodies. Herein, "specificity" means the antibodies can bind to hLRTM4 gene products or fragments.

The present invention not only includes intact monoclonal antibodies or polyclonal antibodies, but also includes antibody fragments with immunoactivity, such as Fab' or (Fab)$_2$ fragments, heavy chains, light chains or chimeric antibodies.

The antibodies in the present invention can be prepared by various techniques known in the art. For example, purified hLRTM4 gene products or its fragments with antigenicity can be used to immunize animals (rabbits, mice, etc.) to induce the generation of polyclonal antibodies. Many adjuvants can be used to improve immune response, including (but not limit to) Freund's adjuvant. Monoclonal antibodies can be generated by hybridoma technique. Antibodies to hLRTM4 can be used to detect hLRTM4 protein in biopsy samples by immunohistochemical analysis. Experiments of the present invention has proved that hLRTM4 can be used as a molecular marker for hepatocellular carcinoma diagnosis.

The present invention also includes oligonucleotides (including antisense RNA and DNA) and ribozymes which inhibit hLRTM4 mRNA. Antisense RNA/DNA and ribozymes can be obtained by any established RNA or DNA synthesis techniques, like the widely applied solid-phase phosphoramidite chemical synthesis method. Antisense RNA can be produced by in vitro or in vivo transcription from the DNA sequence with encodes this RNA. Preferred small interfering double-strand RNAs has the corresponding sequences of LRTM4 nucleotide sequence, usually 17-23 bp, preferably 19-21 by in length, with a 3'-terminal dtdt sequence.

The proteins of the present invention can be used to screen for substances interacting with hLRTM4 protein (e.g. receptors, inhibitors, agonist or antagonist etc.) by various ordinary screening methods.

In a preferred example, LRTM4 protein can be used to screen for drugs that inhibit HCC cell proliferation. hLRTM4 proteins are used to screen Optima RNA library, the obtained specific Optimas which combine to hLRTM4 protein can be isolated and largely prepared. Then, the Optima is introduced into HCC cells to further study the effects of these small molecular drugs on hLRTM4 protein at cell level. For example, these small molecular drugs are added into the medium of cultured cells which highly express hLRTM4 protein (like 7404/LR+ cells) so as to analyze their effects on cell proliferation by MTT method. 7404 cells were used as a control. Further, the Optima RNA is screened for moleculars which inhibit 7404/LR+ cell proliferation. These Optima RNAs are potential anti-tumor drugs.

The proteins of the present invention and its antibodies, inhibitors, agonists, antagonists or receptors, can provide different effects while administered in treatments. For example, hLRTM4 can promote liver regeneration and liver injury repair, while the antisense nucleic acid fragments and antibodies of hLRTM4 can inhibit tumor growth by inhibiting the expression and activity of hLRTM4. Generally, these materials are formulated in nontoxic, inert and pharmaceutically acceptable aqueous medium, although pH changes according to the characters of formulated materials and diseases to be treated, generally pH 5-8, preferably pH 6-8. The formulated pharmaceutical composition is administrated in conventional routes including, but not limited to, intramuscular, intravenous, intraperitoneal, subcutaneous, intracutaneous or topical administration.

The polypeptides of the present invention can be directly used for disease therapy, such as the treatment to repair injured liver. Other pharmaceutical agents, such as hepatocyte growth factor (HGF), can be used in combination with the hLRTM4 protein.

The present invention also provides a pharmaceutical composition, which comprises safe and effective amount of hLRTM4 polypeptides or its agonists, antagonists (such as antisense nucleic acids or antibodies) in combination with a pharmaceutically acceptable carrier. Such a carrier includes but is not limited to saline, buffer solution, glucose, water, glycerin, ethanol, or the combination thereof. The pharmaceutical formulation should be suitable for delivery method. The pharmaceutical composition may be in the form of injections which are made by conventional methods, using physiological saline or other aqueous solution containing glucose or auxiliary substances. The pharmaceutical compositions in the form of tablet or capsule may be prepared by routine methods. The pharmaceutical compositions, e.g., injections, solutions, tablets, and capsules, should be manufactured under sterile conditions. The active ingredient is administrated in therapeutically effective amount, e.g., about 1 ug-5 mg/kg body weight per day. Moreover, the polypeptide of invention can be administrated together with other therapeutic agents.

When using pharmaceutical composition, the safe and effective amount of the HLRTM4 protein or its antagonist or agonist is administered to mammals. Typically, the safe and effective amount is at least about 10 ug/kg body weight and less than about 8 mg/kg body weight in most cases, and preferably about 10 ug-1 mg/kg body weight. Certainly, the precise amount depends upon various factors, such as delivery methods, the subject health, etc., and is within the judgment of the skilled clinician.

The present invention also relates to methods to quantitatively or in situ detect the expression of the hLRTM4 protein. These assays are well-known in the art, including FISH assay and radioimmunoassay. The determined expression level of hLRTM4 protein can be used to diagnose hLRTM4 protein related diseases like HCC.

One way to detect the presence of LRTM4 protein is to use hLRTM4-specific antibodies. It includes: contacting the sample with the antibody specifically against hLRTM4 protein; observing the formation of antibody complex which indicates the presence of hLRTM4 protein in the sample.

Furthermore, part or full-length hLRTM4 polynucleotides can be immobilized as probes on microarray or DNA chip (also known as "gene chip") to analyze the differential expression in tissues and gene diagnosis. Specific primers of hLRTM4 protein can be used to detect hLRTM4 transcripts by RT-PCR amplification.

In an example of the present invention, the expression pattern of hLRTM4 gene in several normal liver and HCC cell lines (BEL-7404, SMMC-7721, L-02, HepG2) was analyzed by RT-PCR. hLRTM4 gene was found to be highly expressed in HCC cell lines (BEL-7404, HepG2), moderately expressed in hepatoma cell lines (SMMC-7721), and undetectable in normal liver cell line (L-02). In addition, hLRTM4 gene was found to be highly expressed in hepatoma, gastric adenocarcinoma and stomach adenocarcinoma cell lines, and undetectable in skin carcinoma, lung carcinoma and tongue squamous cancer cell lines. The results proved that hLRTM4 gene was specifically overexpressed in digestive tract cancers. RT-PCR analysis of HCC and corresponding adjacent noncancerous tissues revealed that hLRTM4 gene was highly expressed in 3 of 7 samples of HCC tissues, as compared with adjacent noncancerous tissues. The result suggested that hLRTM4 gene was overexpressed in cancerous tissues. It is closely related to digestive tract cancers and can be further developed as a molecular marker of cancer.

In another example, sense or antisense hLRTM4 gene was transfected into HCC cell lines. The result proved that hLRTM4 gene was associated with cell proliferation. Transfecting antisense hLRTM4 gene inhibited the growth of HCC cells. Antisense hLRTM4 gene administration also inhibited tumor growth in nude mice xenograft model. Thus, antagonists to hLRTM4, like antisense nucleic acid molecules, can be developed as anti-tumor agents.

In another example, hLRTM4 gene is proved to promote liver regeneration and recovery of injured liver. Thus, hLRTM4 and its agonists can be developed as liver regeneration promoting agents.

The main advantages of the present invention are: the novel liver regeneration associated protein hLRTM4 can regulate hepatocyte proliferation and be used to repair liver injury. Furthermore, since the protein abnormally overexpresses in HCC and other cancer cells, it can be used as a diagnosis marker of HCC and other cancers. Drugs or agents, which inhibit the abnormal overexpression of hLRTM4 protein, can inhibit the malignant proliferation of tumor cells. The tumor inhibitors provided by the present invention, including antisense nucleic acids and antibodies of hLRTM4, are new biological agents with high specificity.

The invention is further illustrated by the following examples. It is appreciated that these examples are only intended to illustrate the invention, but not to limit the scope of the invention. For the experimental methods in the following examples, they are performed under routine conditions, e.g., those described by Sambrook. et al., in Molecule Clone: A Laboratory Manual, New York: Cold Spring Harbor Laboratory Press, 1989, or as instructed by the manufacturers, unless otherwise specified.

EXAMPLE 1

Cloning of hLRTM4 Gene

A pair of specific primers were synthesized which had the follow sequences:

```
                                            (SEQ ID NO: 3)
5' primer sequence: 5'-GTCGTACCACCCCAGAATGT-3'

(SEQ ID NO: 4)
3' primer sequence: 5'-TTTAAACGGGTCCATCTCCC-3',
```

The coding sequence of hLRTM4 gene was amplified from human liver cDNA library (GIBCO Int.) by PCR amplification, then cloned into pMD18-T plasmid (TaKaRa Co.) to construct pThLRTM4 clone. After sequencing (Bioasia Co.), the DNA sequence of obtained hLRTM4 gene was shown as follows:

```
                                                                 (SEQ ID NO: 1)
TCGTACCACC CCAGA ATG TG CACTGGAGGC TGTGCCAGAT GCCTGGGGGG GACCCTCATT    60

CCCCTTGCTT TTTTTGGCTT CCTGGCTAAC ATCCTGTTAT TTTTTCCTGG AGGAAAAGTG    120

ATAGATGACA ACGACCACCT TTCCCAAGAG ATCTGGTTTT TCGGAGGAAT ATTAGGAAGC    180
```

```
                                                   -continued
GGTGTCTTGA TGATCTTCCC TGCGCTGGTG TTCTTGGGCC TGAAGAACAA TGACTGCTGT    240

GGGTGCTGCG GCAACGAGGG CTGTGGGAAG CGATTTGCGA TGTTCACCTC CACGATATTT    300

GCTGTGGTTG GATTCTTGGG AGCTGGATAC TCGTTTATCA TCTCAGCCAT TTCAATCAAC    360

AAGGGTCCTA AATGCCTCAT GGCCAATAGT ACATGGGGCT ACCCCTTCCA CGACGGGGAT    420

TATCTCAATG ATGAGGCCTT ATGGAACAAG TGCCGAGAGC CTCTCAATGT GGTTCCCTGG    480

AATCTGACCC TCTTCTCCAT CCTGCTGGTC GTAGGAGGAA TCCAGATGGT TCTCTGCGCC    540

ATCCAGGTGG TCAATGGCCT CCTGGGGACC CTCTGTGGGG ACTGCCAGTG TTGTGGCTGC    600

TGTGGGGGAG ATGGACCCGT TTAAA                                          625
```

The encoded hLRTM4 protein had the following amino acid sequence:

```
                                                          (SEQ ID NO: 2)
MCTGGCARCL GGTLIPLAFF GFLANILLFF PGGKVIDDND HLSQEIWFFG GILGSGVLMI     60

FPALVFLGLK NNDCCGCCGN EGCGKRFAMF TSTIFAVVGF LGAGYSFIIS AISINKGPKC    120

LMANSTWGYP FHDGDYLNDE ALWNKCREPL NVVPWNLTLF SILLVVGGIQ MVLCAIQVVN    180

GLLGTLCGDC QCCGCCGGDG PV                                            202
```

EXAMPLE 2

Construction of Expression Strain of hLRTM4 Fusion Protein in E. coli pThLRTM4 plasmid containing the entire coding sequence for hLRTM4 was prepared as described in Example 1, and digested with restriction enzymes EcoRI and XhoI. The EcoRI-XhoI DNA fragment containing the entire coding sequence for hLRTM4 was isolated and ligated into pGEX-4T1 vector (Amersham Pharmacia Co.) to construct pGEXLR plasmid. Competent E. coli strain BL21-DE3 cells were transformed with pGEXLR plasmid. The ampicillin-resistance transformants were amplified and screened for clones containing plasmids which specifically highly expressed GST-hLRTM4 fusion protein. The plasmids of corresponding transformants were isolated and examined by restriction enzyme digestion. DNA sequences were confirmed by direct DNA sequence analysis.

To produce hLRTM4 protein, the identified pGEXLR transformants were inoculated into 1 liter 2×YT medium by ratio 1:100. After incubation for 3 hours at 37° C. in a shaking incubator, the culture was added IPTG to a final concentration of 0.25 mmol/L. After further incubation for 3 hours, the cell pellet was collected by centrifugation (4000 rpm, 10 min). The pellet was washed by PBS once, then resuspended in 25 ml PBS containing 1 mmol/L PMSF, and lysed by sonication. 10% Triton X-100 was added to a final concentration of 1%, the lysate was centrifuged at 10,000 rpm for 10 min. The supernatant was removed and purified by glutathione-Sepharose affinity chromatography. The glutathione-Sepharose column was equilibrated with PBS (containing 1% Triton X-100, 100 mmol/L DTT, 1 mmol/L PMSF). The supernatant of cell lysate was applied to the column. After washing the column with 10 column volumes of PBS, the glutathione-Sepharose adsorbed GST-hLRTM4 protein was eluted with 3 column volumes of 50 mmol/L Tris.Cl, pH 8.0, containing 5 mmol/L glutathione. The eluted fraction was collected and lyophilized.

The purified GST-hLRTM4 fusion protein was obtained and its molecular weight was about 48 kDa.

EXAMPLE 3

Preparation of Anti-hLRTM4 Antibody

The second extracellular domain of hLRTM4 gene was amplified by PCR with pThLRTM4 plasmid as template, the primers are:

```
                                            (SEQ ID NO: 5)
5' primer: 5'-CATATGGGGAAGCGATTTGCGATGT-3'

(SEQ ID NO: 6)
3' primer: 5'-CTCGAGGACCAGCAGGATGGAGAA-3',
```

The PCR amplification product containing the second extracellular domain (SEQ ID NO:1 from 265 to 510) of hLRTM4 gene was digested by NdeI and XhoI, then cloned into pET24a vector (Novagen Co.) to construct pET24a-EC2 plasmid. Competent E. coli strain BL21-DE3 cells were transformed with pET24a-EC2 plasmid, ampicillin-resistance transformants were amplified and screened for clones which specifically highly expressed GST-hLRTM4-EC2 fusion protein. The plasmids of corresponding transformants were isolated and examined by restriction enzyme digestion. DNA sequences were confirmed by direct DNA sequence analysis.

The ensured transformants were inoculated into 1 liter 2×YT medium by ratio 1:100. After incubation for 3 hours at 37° C. in a shaking incubator, the culture was added IPTG to a final concentration of 0.25 mmol/L. After further incubation for 3 hours, the cell pellet was collected by centrifugation (4,000 rpm, 10 min) and then lysed by sonication. After adding 10% Triton X-100 to a final concentration of 1%, the lysate was centrifuged at 10,000 rpm for 10 min. The supernatant was removed and purified by glutathione-Sepharose affinity chromatography.

Male New Zealand white rabbits weighing 2.5 kg were used in immunization for preparing antisera. For immunization, an emulsion was prepared by mixing an equal volume of purified GST-hLRTM4-EC2 protein (400 ug/mL) and Freud's complete adjuvant. Two rabbits were immunized subcutaneously. One week later, the rabbits were re-immunized twice at one week intervals with 1 ml of emulsion of same protein amount and Freud's incomplete adjuvant per injection. The first bleeding was taken from ear vein, and the potency of antiserum was determined by ELISA. Once the potency of antiserum met the requirement, whole blood was harvested from carotid 10 days after the final immunization and serum was isolated. After adding $NaN_3$ to a final concentration of about 0.1%, antiserum was stored at −20° C.

EXAMPLE 4

Detection of Expression of hLRTM4 Gene in Different Cell Lines

The following 13 different human cell lines in common use were analyzed: poorly differentiated stomach adenocarcinoma MKN45, stomach adenocarcinoma cell line BGC-823, lung epithelial cell line A549, skin carcinoma squamous cell line A431, tongue squamous cancer cell line Tca-8113, bone marrow neuroblastoma cell line SK-N-SH, skin malignant melanoma cell line A375, gastric adenocarcinoma cell line SGC-7901, cervical cancer cell line HeLa, hepatoma cells (BEL-7404, HepG2 and SMMC-7721), and normal liver cell L-02.

Total RNAs of different cell lines were isolated by using TRIZOL kit (GIBCO/BRL Int.) according to manufacturer's instruction, and were reverse-transcribed to prepare cDNA templates. The products were used for PCR to detect hLRTM4 gene with the same primers as Example 1: 5'-GTC GTA CCA CCC CAG AAT GT-3' (SEQ ID NO:3) and 5'-TTT AAA CGG GTC CAT CTC CC-3' (SEQ ID NO:4). An initial denaturation step at 94° C. for 2 min was followed by 30 cycles of denaturation at 94° C. for 30 sec, annealing at 55° C. for 30 sec and extension at 72° C. for 90 sec. After the amplification, a final extension step was performed at 72° C. for 5 min. The internal control GAPDH was amplified with specific primers (GAPDHL: 5'-ACC ACA GTC CAT GCC ATC AC-3' (SEQ ID NO:7); GAPDHR: 5'-TCC ACC ACC CTG TTG CTG TA-3' (SEQ ID NO:8)). An initial denaturation step at 94° C. for 2 min was followed by 25 cycles of denaturation at 94° C. for 30 sec, annealing at 55° C. for 30 sec and extension at 72° C. for 90 sec. After the amplification, a final extension step was performed at 72° C. for 5 min. The PCR products of hLRTM4 and GAPDH were electrophoresed simultaneously to determine the difference of hLRTM4 expression in different human cell lines.

Figure 1:
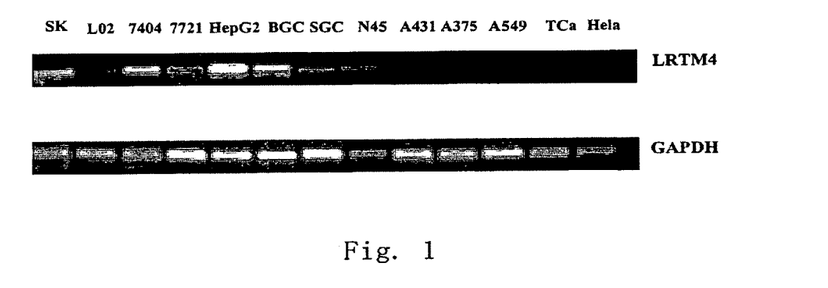
FIG. 1 shows the RT-PCR results of hLRTM4 expression pattern in different cell lines. SK-N-SH, bone marrow neuroblastoma cell; L-02, normal liver cell; BEL-7404, hepatoma cell; SMMC-7721, hepatoma cell; HepG2, hepatocellular carcinoma cell; BGC-823, stomach adenocarcinoma cell; SGC-7901, gastric adenocarcinoma cell line; MKN-45, poorly differentiated stomach adenocarcinoma cell; A431, skin carcinoma squamous cell; A375, skin malignant melanoma cell; A549, lung epithelial cell; Tca-8113, tongue squamous cancer cell; HeLa, cervical cancer cell. GAPDH gene was amplified as a control.

As shown in FIG. 1, hLRTM4 gene was expressed in liver cells (BEL-7404, SMMC-7721, HepG2), gastric carcinoma cells (MKN-45, BGC-823, SGC-7901) and neuroblastoma cell SK-N-SH, and unexpressed in other cell lines. The results indicated that the expression of hLRTM4 gene had a certain extent of tissue specificity. hLRTM4 gene was hardly expressed in normal liver cell L-02, moderately express in hepatoma cell SMMC-7721, and was highly expressed in hepatocellular carcinoma cells BEL-7404 and HepG2. The results suggested that hLRTM4 gene was a potential marker for tumor diagnosis.

EXAMPLE 5

Detection of hLRTM4 Expression in HCC Samples

Seven pairs of HCC (K or C) and adjacent noncancerous tissues (N, P or L) samples, 135K and 135L, 1055C and 1055P, 183K and 183L, 58C and 58N, 152K and 152L, 158K and 158L, 1049C and 1049P, were analyzed for hLRTM4 expression. Total RNAs of different samples were isolated by using TRIZOL kit (GIBCO/BRL Int.) according to manufacturer's instruction, and were reverse-transcribed to prepare cDNA templates. The products were used for PCR to detect hLRTM4 gene with the same primers as Example 4. An initial denaturation step at 94° C. for 2 min was followed by 30 cycles of denaturation at 94° C. for 30 sec, annealing at 55° C. for 30 sec and extension at 72° C. for 90 sec. After the amplification, a final extension step was performed at 72° C. for 5 min. The internal control GAPDH was amplified with same specific GAPDH primers as Example 4. The PCR products of hLRTM4 and GAPDH were electrophoresed simultaneously to determine the differential expression of hLRTM4.

Figure 2:
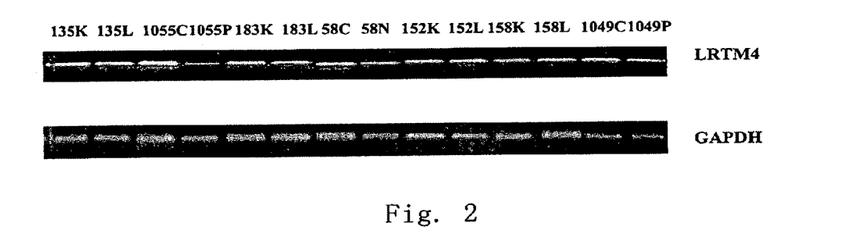
FIG. 2 shows the RT-PCR results of hLRTM4 expression pattern in HCC and corresponding adjacent noncancerous tissues. 135K, 1055C, 183K, 58C, 152K, 158K and 1049C refer to cancerous liver tissues; 135L, 1055P, 183L, 58N, 152L, 158L and 1049P refer to corresponding adjacent noncancerous liver tissues. GAPDH gene was amplified as a control.
Figure 3:
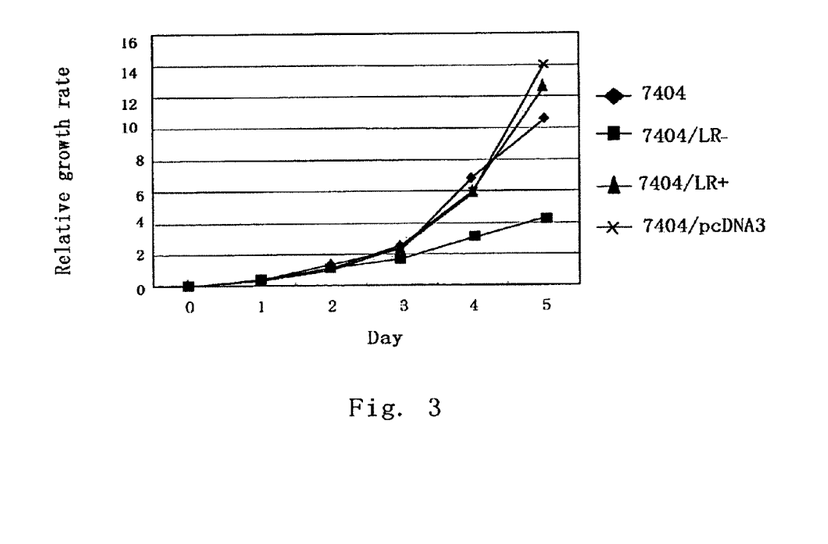
FIG. 3 shows that the antisense polynucleotide of hLRTM4 gene inhibits the proliferation of hepatoma cells.

As shown in FIG. 2, hLRTM4 gene was highly expressed in HCC tissues 183K, 58C and 1049C, as compared with corresponding adjacent noncancerous tissues 183L, 58N and 1049P. The expression of internal control GAPDH was almost the same. The result elucidated that hLRTM4 gene was specifically and highly expressed in tumor tissues and could be used as a marker of HCC.

EXAMPLE 6

Inhibition of HCC Cell Proliferation by hLRTM4 Antisense Nucleic Acid

The sense and antisense expression plasmids of hLRTM4 gene were constructed as follows: the coding sequence of hLRTM4 gene (SEQ ID NO:1 from nucleotide 16 to 625) was inserted into the EcoRI and HindIII sites of pcDNA3 vector to construct pcDNA3LR+ plasmid; hLRTM4 gene was inversely inserted into the XhoI and BamHI site of pcDNA3 vector to construct pcDNA3LR− plasmid.

pcDNA3LR+ and pcDNA3LR− plasmids were respectively transfected into BEL-7404 and L02 cells by LipofectAMINE reagent (7404 cells express hLRTM4 gene, L02 cells don't express hLRTM4 gene). The stable transfectants were selected by G418, the resistant cell clones were amplified. At the same time, the untransfected wild type cells and cells transfected with empty vector pcDNA3 were used as controls. 2 series of stable transfected cells were obtained: 7404, 7404/pcDNA3, 7404/LR+ and 7404/LR− cells; L02, L02/pcDNA3, L02/LR+ and L02/LR− cells.

Cell proliferation rate was measured by 3-[4,5-dimethylthiazol-2-yl]-2,5-diphenyltetrazolium bromide (MTT) method. 7404, 7404/pcDNA3, 7404/LR+, 7404/LR− cells were seeded at $5\times10^3$ cells/well in 24-well plate after 24 h synchronization in serum-free medium. Cell growth was measured by MTT assay during 8 days (n=6). 7404/LR− cells showed obvious lower proliferative activity as compared to control cells (7404 and 7404/pcDNA3). However, the proliferation rates of L02, L02/pcDNA3, L02/LR+, L02/LR− cells were not evidently different. The results suggested that antisense hLRTM4 nucleic acid could inhibit HCC cell proliferation.

EXAMPLE 7

Inhibition of Tumor Growth by Antisense hLRTM4 in Nude Mice Model 5-week-old nude mice were subcutaneously injected with $2\times10^6$ hepatoma cells BEL-7404 each to generate the nude mice tumorgenerous models. One week later, pcDNA3LR+ and pcDNA3LR− plasmids were introduced into mice through tail vein injection, 50 ug plasmid every time, every 3 days. The mice were sacrificed 3 weeks later, and the tumors were isolated and photographed.

Figure 4:
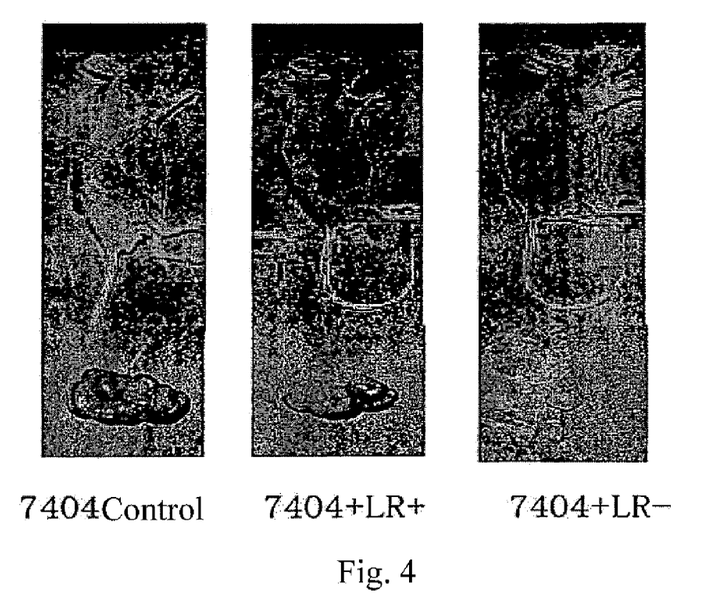
FIG. 4 shows the effect of antisense sequence of hLRTM4 gene on nude mice xenograft model.

As shown in FIG. 4, the tumors of nude mice injected with pcDNA3LR− plasmid were obviously smaller than those of control group. The results indicated that pcDNA3LR− plasmid containing antisense hLRTM4 gene could inhibit tumor growth and could be a potential anti-tumor drug.

EXAMPLE 8

Promotion Effects of hLRTM4 on Liver Regeneration and Recovery of Injured Liver

The result of this Example approved that hLRTM4 could be used to promote liver regeneration and repair liver injury.

Acute $CCl_4$ liver injury was induced by i.p. injection of a single 0.5 ml/kg weight and 1 ml/kg weight of a 40% (V/V) solution of $CCl_4$ in plant oil. 200 ug pcDNA3 recombinant plasmid containing the coding sequence of LRTM4 and 50 ul SA liposome (2 mg/mL) was mixed with 500 ul PBS respectively, and the two solutions were combined. The hLRTM4 gene-liposome complex was transferred into rat through tail vein injection 24 h after $CCl_4$-injury. The rats were sacrificed 72 hours after injury. Livers and serum were harvested.

To determine the expression level of hLRTM4 gene, RT-PCR was performed as Example 4. Total RNAs of liver tissues were isolated by TRIZOL kit (GIBCO/BRL Co.) as manufacturer's manual. hLRTM4 gene and internal control GAPDH gene were amplified by PCR. The PCR products of LRTM4 and GAPDH were electrophoresed and quantitated. The normalized results of LRTM4/GAPDH were taken as the expression level of LRTM4.

To determine the injury extent of liver, the GPT level in serum was analyzed by Transaminase Quantitative Kit (Sigma Inc.) according to manufacturer's manual: pipette 100 ul Alanine-a-KG substrate into a test tube, place in 37° C. water bath to warm, add 20 ul serum, shake gently to mix, leave in water bath for 30 min, add 100 ul Sigma Color reagent, shake gently and leave at room temperature for 20 min, add 1 ml 0.4 mol/L sodium hydroxide solution, mix by inversion, wait at least 5 min more, read and record absorbance using water as reference at 505 nm. Prepare the calibration curve as suggested, determine the GPT activity in Sigma-Frankel [SF] Units/ml from the calibration curve.

Figure 5:
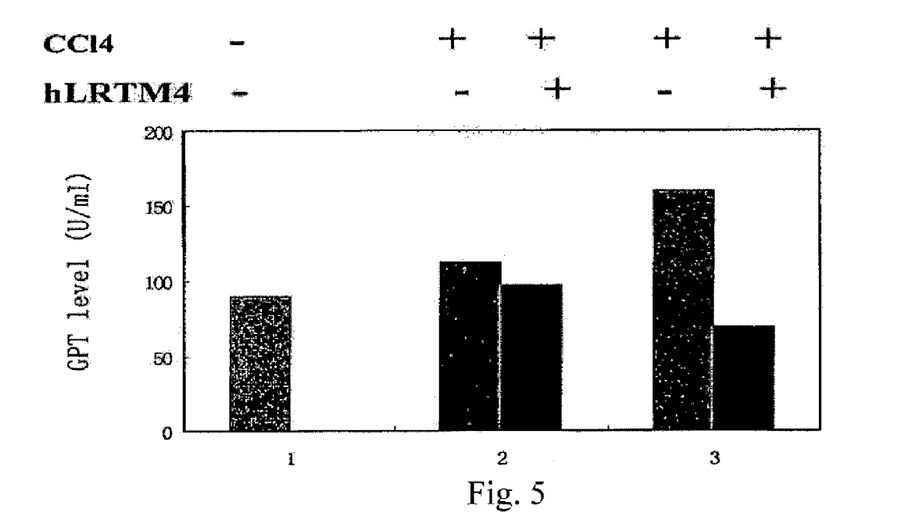
FIG. 5 shows that hLRTM4 promotes liver regeneration in rat $CCl_4$-injury model.

As shown in FIG. 5, Group 1, normal rats; group 2, rats administrated with 0.5 ml $CCl_4$ kg body weight; group 3, rats administrated with 1 ml $CCl_4$/kg body weight. In group 2 and group 3, the black columns indicated the introduction of hLRTM4 gene. Results elucidated that the level of glutamate pyruvate transaminase (GPT) was low in normal liver tissues; but raised after $CCl_4$ administration in a dose dependent manner. After the introduction of hLRTM4 gene, the GPT level decreased. These results suggested that hLRTM4 gene was effective in repairing liver injury.

As described above, hLRTM4 protein is a novel human liver regeneration associated protein.

EXAMPLE 9

Small Interference RNA of hLRTM4 Inhibits HCC Cell Proliferation

Double strand RNA fragments were designed and synthesized according to hLRTM4 gene sequence, and introduced into HCC cells BEL-7404. The endogenous homogenous hLRTM4 RNAs were degraded by these small interfering RNAs and the proliferation of HCC cells BEL-7404 was inhibited.

Some small interfering RNA sequences were mentioned as follows (only the sense strand):

|  | Sequence | SEQ ID NO: |
|---|---|---|
| dsRNA1* | 5'-ggaagcggugucuugaugauc-3' | 9 |
| dsRNA2* | 5'-gggaagcgauuugcgauguuc-3' | 10 |
| dsRNA3* | 5'-ggaacaagugccgagagccuc-3' | 11 |
| dsRNA4* | 5'-gggugcugcggcaacgagggc-3' | 12 |
| dsRNA5* | 5'-guuuaaaccuccgagaugagc-3' | 13 |

*with 3'-terminal dtdt

Methods: 50 ng synthesized double-strand RNA was mixed with LipofectAMINE reagent (Life Technologies, GibcoBRL) and transfected into BEL-7404 cells. 72 hours after transfection, BEL-7404 and BEL-7404/LRTM4-RNAi cells were seeded into 24-well plate at $5 \times 10^3$ cells/well after 24 hours synchronized in serum-free DMEM medium. Cell proliferation rate was measured using a 3-[4,5-dimethylthiazol-2-yl]-2,5-diphenyltetrazolium bromide (MTT) method during 8 days. The result indicated that the proliferation rate of BEL-7404/LRTM4-RNAi cells was obviously lower as compared with control cells.

All the documents cited herein are incorporated into the invention as reference, as if each of them is individually incorporated. Further, it would be appreciated that, in the above teaching of the invention, the skilled in the art could make certain changes or modifications to the invention, and these equivalents would still be within the scope of the invention defined by the appended claims of the present application.

What is claimed is:

1. A method for treating carcinoma, comprising administering to a subject a preparation comprising an antagonist of hLRTM4 gene or gene product, wherein the hLRTM4 gene has the sequence of SEQ ID NO: 1, wherein the antagonist is an antibody against hLTRM4 protein, an antisense polynucleotide or a small interfering double-strand RNA, and wherein the carcinoma is a hepatocellular carcinoma, wherein the antisense polynucleotide or the small interfering double-stranded RNA are capable of binding to the sequence of SEQ ID NO: 1 or the complementary sequence thereof.

2. The method of claim 1, wherein the antagonist is an antisense polynucleotide to the hLRTM4 gene product, wherein the antisense polynucleotide having a contiguous fragment of at least 15 bases that hybridizes to the hLRTM4 gene transcript.

3. The method of claim 2, wherein the antisense polynucleotide is 15-625 nucleotides long.

4. The method of claim 1, wherein the antagonist is a small interfering double-strand RNA for the hLRTM4 gene product, wherein the interfering double-strand RNA is 17-23 by long.

5. The method of claim 4, wherein the interfering double-strand RNA is 19-21 by long.

6. The method of claim 4, wherein the interfering double-strand RNA further comprises a 3'-terminal dTdT sequence.

7. The method of claim 5, where in the interfering double-strand RNA further comprises a 3'-terminal dTdT sequence.

8. The method of claim 1, wherein the carcinoma is hepatocellular carcinoma.

* * * * *

SEQUENCE LISTING

```
<160> NUMBER OF SEQ ID NOS: 13

<210> SEQ ID NO 1
<211> LENGTH: 625
<212> TYPE: DNA
<213> ORGANISM: Homo sapiens

<400> SEQUENCE: 1
tcgtaccacc ccaga atg tgc act gga ggc tgt gcc aga tgc ctg ggg ggg      51
                Met Cys Thr Gly Gly Cys Ala Arg Cys Leu Gly Gly
                 1               5                  10
```

```
acc ctc att ccc ctt gct ttt ttt ggc ttc ctg gct aac atc ctg tta      99
Thr Leu Ile Pro Leu Ala Phe Phe Gly Phe Leu Ala Asn Ile Leu Leu
        15                  20                  25 ttt ttt cct gga gga aaa gtg ata gat gac aac gac cac ctt tcc caa     147
Phe Phe Pro Gly Gly Lys Val Ile Asp Asp Asn Asp His Leu Ser Gln
        30                  35                  40 gag atc tgg ttt ttc gga gga ata tta gga agc ggt gtc ttg atg atc     195
Glu Ile Trp Phe Phe Gly Gly Ile Leu Gly Ser Gly Val Leu Met Ile
45                  50                  55                  60 ttc cct gcg ctg gtg ttc ttg ggc ctg aag aac aat gac tgc tgt ggg     243
Phe Pro Ala Leu Val Phe Leu Gly Leu Lys Asn Asn Asp Cys Cys Gly
                65                  70                  75 tgc tgc ggc aac gag ggc tgt ggg aag cga ttt gcg atg ttc acc tcc     291
Cys Cys Gly Asn Glu Gly Cys Gly Lys Arg Phe Ala Met Phe Thr Ser
            80                  85                  90 acg ata ttt gct gtg gtt gga ttc ttg gga gct gga tac tcg ttt atc     339
Thr Ile Phe Ala Val Val Gly Phe Leu Gly Ala Gly Tyr Ser Phe Ile
                95                  100                 105 atc tca gcc att tca atc aac aag ggt cct aaa tgc ctc atg gcc aat     387
Ile Ser Ala Ile Ser Ile Asn Lys Gly Pro Lys Cys Leu Met Ala Asn
        110                 115                 120 agt aca tgg ggc tac ccc ttc cac gac ggg gat tat ctc aat gat gag     435
Ser Thr Trp Gly Tyr Pro Phe His Asp Gly Asp Tyr Leu Asn Asp Glu
125                 130                 135                 140 gcc tta tgg aac aag tgc cga gag cct ctc aat gtg gtt ccc tgg aat     483
Ala Leu Trp Asn Lys Cys Arg Glu Pro Leu Asn Val Val Pro Trp Asn
                145                 150                 155 ctg acc ctc ttc tcc atc ctg ctg gtc gta gga gga atc cag atg gtt     531
Leu Thr Leu Phe Ser Ile Leu Leu Val Val Gly Gly Ile Gln Met Val
            160                 165                 170 ctc tgc gcc atc cag gtg gtc aat ggc ctc ctg ggg acc ctc tgt ggg     579
Leu Cys Ala Ile Gln Val Val Asn Gly Leu Leu Gly Thr Leu Cys Gly
        175                 180                 185 gac tgc cag tgt tgt ggc tgc tgt ggg gga gat gga ccc gtt taaa       625
Asp Cys Gln Cys Cys Gly Cys Cys Gly Gly Asp Gly Pro Val
        190                 195                 200

<210> SEQ ID NO 2
<211> LENGTH: 202
<212> TYPE: PRT
<213> ORGANISM: Homo sapiens

<400> SEQUENCE: 2

Met Cys Thr Gly Gly Cys Ala Arg Cys Leu Gly Gly Thr Leu Ile Pro
1               5                   10                  15

Leu Ala Phe Phe Gly Phe Leu Ala Asn Ile Leu Leu Phe Phe Pro Gly
            20                  25                  30

Gly Lys Val Ile Asp Asp Asn Asp His Leu Ser Gln Glu Ile Trp Phe
        35                  40                  45

Phe Gly Gly Ile Leu Gly Ser Gly Val Leu Met Ile Phe Pro Ala Leu
    50                  55                  60

Val Phe Leu Gly Leu Lys Asn Asn Asp Cys Cys Gly Cys Cys Gly Asn
65                  70                  75                  80

Glu Gly Cys Gly Lys Arg Phe Ala Met Phe Thr Ser Thr Ile Phe Ala
            85                  90                  95
```

```
Val Val Gly Phe Leu Gly Ala Gly Tyr Ser Phe Ile Ile Ser Ala Ile
            100                 105                 110

Ser Ile Asn Lys Gly Pro Lys Cys Leu Met Ala Asn Ser Thr Trp Gly
        115                 120                 125

Tyr Pro Phe His Asp Gly Asp Tyr Leu Asn Asp Glu Ala Leu Trp Asn
130                 135                 140

Lys Cys Arg Glu Pro Leu Asn Val Val Pro Trp Asn Leu Thr Leu Phe
145                 150                 155                 160

Ser Ile Leu Leu Val Val Gly Gly Ile Gln Met Val Leu Cys Ala Ile
                165                 170                 175

Gln Val Val Asn Gly Leu Leu Gly Thr Leu Cys Gly Asp Cys Gln Cys
            180                 185                 190

Cys Gly Cys Cys Gly Gly Asp Gly Pro Val
        195                 200

<210> SEQ ID NO 3
<211> LENGTH: 20
<212> TYPE: DNA
<213> ORGANISM: Artificial sequence
<220> FEATURE:
<221> NAME/KEY: misc_feature
<222> LOCATION: (1)..(20)
<223> OTHER INFORMATION: primer

<400> SEQUENCE: 3
gtcgtaccac cccagaatgt                                                   20

<210> SEQ ID NO 4
<211> LENGTH: 20
<212> TYPE: DNA
<213> ORGANISM: Artificial sequence
<220> FEATURE:
<221> NAME/KEY: misc_feature
<222> LOCATION: (1)..(20)
<223> OTHER INFORMATION: primer

<400> SEQUENCE: 4
tttaaacggg tccatctccc                                                   20

<210> SEQ ID NO 5
<211> LENGTH: 25
<212> TYPE: DNA
<213> ORGANISM: Artificial sequence
<220> FEATURE:
<221> NAME/KEY: misc_feature
<222> LOCATION: (1)..(25)
<223> OTHER INFORMATION: primer

<400> SEQUENCE: 5
catatgggga agcgatttgc gatgt                                             25

<210> SEQ ID NO 6
<211> LENGTH: 24
<212> TYPE: DNA
<213> ORGANISM: Artificial sequence
<220> FEATURE:
<221> NAME/KEY: misc_feature
<222> LOCATION: (1)..(24)
<223> OTHER INFORMATION: primer

<400> SEQUENCE: 6
ctcgaggacc agcaggatgg agaa                                              24

<210> SEQ ID NO 7
<211> LENGTH: 20
```

```
<212> TYPE: DNA
<213> ORGANISM: Artificial sequence
<220> FEATURE:
<221> NAME/KEY: misc_feature
<222> LOCATION: (1)..(20)
<223> OTHER INFORMATION: primer

<400> SEQUENCE: 7
accacagtcc atgccatcac                                              20

<210> SEQ ID NO 8
<211> LENGTH: 20
<212> TYPE: DNA
<213> ORGANISM: Artificial sequence
<220> FEATURE:
<221> NAME/KEY: misc_feature
<222> LOCATION: (1)..(20)
<223> OTHER INFORMATION: primer

<400> SEQUENCE: 8
tccaccaccc tgttgctgta                                              20

<210> SEQ ID NO 9
<211> LENGTH: 21
<212> TYPE: RNA
<213> ORGANISM: Artificial sequence
<220> FEATURE:
<221> NAME/KEY: misc_feature
<223> OTHER INFORMATION: double-stranded small RNA

<400> SEQUENCE: 9
ggaagcggug ucuugaugau c                                            21

<210> SEQ ID NO 10
<211> LENGTH: 21
<212> TYPE: RNA
<213> ORGANISM: Artificial sequence
<220> FEATURE:
<221> NAME/KEY: misc_feature
<223> OTHER INFORMATION: double-stranded small RNA

<400> SEQUENCE: 10
gggaagcgau uugcgauguu c                                            21

<210> SEQ ID NO 11
<211> LENGTH: 21
<212> TYPE: RNA
<213> ORGANISM: Artificial sequence
<220> FEATURE:
<221> NAME/KEY: misc_feature
<223> OTHER INFORMATION: double-stranded small RNA

<400> SEQUENCE: 11
ggaacaagug ccgagagccu c                                            21

<210> SEQ ID NO 12
<211> LENGTH: 21
<212> TYPE: RNA
<213> ORGANISM: Artificial sequence
<220> FEATURE:
<221> NAME/KEY: misc_feature
<223> OTHER INFORMATION: double-stranded small RNA

<400> SEQUENCE: 12
gggugcugcg gcaacgaggg c                                            21

<210> SEQ ID NO 13
<211> LENGTH: 21
```

```
<212> TYPE: RNA
<213> ORGANISM: Artificial sequence
<220> FEATURE:
<221> NAME/KEY: misc_feature
<223> OTHER INFORMATION: double-stranded small RNA

<400> SEQUENCE: 13
guuuaaaccu ccgagaugag c                                              21
```